United States Patent
Van Tenac

(10) Patent No.: US 12,040,081 B2
(45) Date of Patent: Jul. 16, 2024

(54) BLISTER PACK STATION

(71) Applicant: ALERTAPACK LTD, Sussex (GB)

(72) Inventor: Phillip John Van Tenac, Sussex (GB)

(73) Assignee: ALERTAPACK LTD, Sussex (GB)

( * ) Notice: Subject to any disclaimer, the term of this patent is extended or adjusted under 35 U.S.C. 154(b) by 741 days.

(21) Appl. No.: 17/138,991

(22) Filed: Dec. 31, 2020

(65) Prior Publication Data

US 2021/0125710 A1 Apr. 29, 2021

Related U.S. Application Data

(63) Continuation-in-part of application No. PCT/IB2019/055676, filed on Jul. 3, 2019.

(51) Int. Cl.
| | | |
|---|---|---|
| *G16H 40/20* | (2018.01) | |
| *A61J 1/03* | (2023.01) | |
| *A61J 7/04* | (2006.01) | |
| *G06K 19/07* | (2006.01) | |
| *G06Q 50/04* | (2012.01) | |
| *G16H 20/10* | (2018.01) | |
| *G16H 20/13* | (2018.01) | |
| *G16H 40/67* | (2018.01) | |
| *G16H 70/40* | (2018.01) | |

(52) U.S. Cl.
CPC ............. *G16H 40/20* (2018.01); *A61J 1/035* (2013.01); *A61J 7/0436* (2015.05); *A61J 7/0481* (2013.01); *G06K 19/0728* (2013.01); *G06Q 50/04* (2013.01); *G16H 20/10* (2018.01); *G16H 20/13* (2018.01); *G16H 40/67* (2018.01); *G16H 70/40* (2018.01); *A61J 2200/30* (2013.01); *A61J 2205/60* (2013.01)

(58) Field of Classification Search
CPC ........ G16H 40/20; G16H 20/10; G16H 20/13; G16H 40/67; G16H 70/40; A61J 1/035; A61J 7/0436; A61J 7/0481; A61J 2200/30; A61J 2205/60; G06K 19/0728; G06Q 50/04
See application file for complete search history.

(56) References Cited

U.S. PATENT DOCUMENTS

2015/0274402 A1* 10/2015 Elliott .................... B65D 83/06
222/23

FOREIGN PATENT DOCUMENTS

| EA | 021376 B1 * | 6/2015 | |
| WO | 2014088692 A2 | 6/2014 | |
| WO | WO-2014088692 A2 * | 6/2014 | ............ A61J 7/0084 |
| WO | 2017130207 A1 | 8/2017 | |
| WO | WO-2017130207 A1 * | 8/2017 | .............. A61J 1/035 |

* cited by examiner

*Primary Examiner* — Curtis A Kuntz
*Assistant Examiner* — James E Munion
(74) *Attorney, Agent, or Firm* — Jose Cherson Weissbrot

(57) ABSTRACT

Embodiments of the present disclosure provide a blister pack station for use with a blister pack. The blister pack station includes at least one slot for receiving at least one blister pack containing one or more tablets. The blister pack station further includes an input module to receive a plurality of instructions from a third party including at least one of an authorized person, a server, a blister pack, and another blister pack station. The blister pack station also includes a chip configured to communicate the plurality of instructions to at least one of a central server, a device based in a cloud network, the blister pack, and the another blister pack station.

20 Claims, 3 Drawing Sheets

BLISTER PACK STATION

TECHNICAL FIELD

The presently disclosed subject matter generally relates to the field of medicine. Particularly, the present subject matter relates to a blister pack station comprising a chip configured to communicate with at least one third party.

BACKGROUND

Millions of people in the world take medicines or vitamin supplements on daily basis for treating one or other diseases or for general wellness. Usually a doctor prescribes these medicines and provides instructions about time for taking the medicines to the patients verbally or in written. Sometimes, the patients have to take more than one medicine in a day at same or different times, Therefore, it becomes difficult for the patients to remember timings and instructions for taking each and every medicine. Also, taking medicines at wrong timing may result in health hazards for the patients.

Another problem these days in the world of medicines is counterfeiting of medicines. These days, most of the medicines available in the market are not authentic/genuine and its almost impossible for the patients to identify whether the medicine is authentic or fake. Consuming the fake medicine or drugs may be hazardous to the health of the patients.

In light of above discussion, there exists need for improved techniques for reminding the patients about the correct timing for taking the medication and also about counterfeiting of the medicines.

SUMMARY

To overcome the above-mentioned limitations and problems, the present disclosure provides a blister pack station comprising at least one slot for holding a pill dispenser or blister pack comprising medicine/pills/tablets. The blister pack station is configured to communicate with at least one third party for receiving instructions and/or for authenticating the stored medicines of the blister pack. The third party may include an authentic person, a server, a cloud application, a computing device, and so forth.

The present disclosure provides a blister pack station capable of receiving and/or storing one or more instructions or information from a third party. The third party can be an authorized person, a server, a computing device like a mobile phone, a smart watch, a hybrid watch, a laptop, a tablet computer, a desktop computer, a personal digital assistant, a smart television, and so forth. In some embodiments, the blister pack station may receive the instruction about the medication like, but not limited to, a timing for taking the tablets, a date of manufacturing of the tablets, a batch information of the tablets, an expiry information of the tablets, manufacturer information, and so forth.

Further, the blister pack station is configured to receive a blister pack or a pill dispenser. The blister pack can be inserted in a slot of the blister pack station for activating the blister pack station. In some embodiments, the blister pack station may receive instructions from a third party and may communicate the stored instructions to the blister pack/pill dispenser. Further, the blister pack station may be configured to transfer these instructions or information to other devices like mobile phones, servers, other blister pack, and the like.

In some embodiments, the blister pack station is configured to fetch blister pack information from a blister pack via wireless or wired means. The blister pack station then may send this information to the third party device like a server (may also be referred as a central server) for fetching additional blister pack information from the server. The blister pack information and the additional blister pack information may be stored in a database of the blister pack station.

The blister pack station is retrofittable and may be configured to receive or connect to any existing blister pack. The blister pack contains a number of tablets.

The blister pack station may store pre-defined information about a plurality of medicines. When a blister pack is connected to or brought near or put into the slot of the blister pack station, then the blister pack station may automatically fetch the blister pack information. Based on the blister pack information, the blister pack station may determine additional blister pack information from the pre-defined information. The pre-defined information may include information like, color, shape, composition, uses, dosage, side effects of the medicines, and so forth.

The present disclosure provides a blister pack station capable of storing one or more instructions or information received from a third party comprising an authentic person. Further, the blister pack station may be configured to arrange or modify the stored information and instructions based on one or more events for example, but not limited to, a time zone, a time when a stored blister pack breaks or opens, and so forth.

The present disclosure provides a blister pack controlling station configured to receive one or more instructions from at least one authorized third party. Further, the blister pack controlling station is configured to transfer or communicate the one or more instructions to another devices comprising blister packs, other blister pack controlling stations, servers, mobile devices, smart watches, laptops, tablet computers, and so forth. Further, the blister pack controlling station can receive any suitable blister pack. In an example, the blister pack may be a plastic blister pack having dimensions of 2 mm×2 mm×50 mm and raised lip that may allow the blister pack to slide down and fix to the blister pack controlling station. In some embodiments, the blister packs may have a hole alongside the lip and the blister pack controlling station may include a latch for locking the pack via the hole into the place and align all the circuit connections to then activate and light up the LEDs or luminescent coating of the blister pack.

The main objective of the present disclosure is to provide a blister pack station, controller, server, application, software/hardware application, and/or a circuit to use with any suitable blister pack-'pill dispenser/tablet package, and the like. Any suitable blister pack with a circuit or/and RFID tag and light emitting diodes and/or luminescent coating may be inserted in the blister pack station for activating the blister pack station. The blister pack may comprise a lip along an edge of the blister pack. In small embodiments, the blister pack may comprise a small hole alongside the lip for a latch of the blister pack station. Further, the blister pack may comprise a chip such as, but not limited to, a Read Only Memory (ROM) chip in the case of a manufacturers production line or an Erasable-Programmable Read Only Memory (EPROM or FRONT) chip where a local pharmacist or doctor may load or seal the blister pack and may need to enter instructions or details onto the chip at the time of packing the blister pack.

The present disclosure provides a blister pack station configured to communicate with a third party for exchanging information and instruction about medication and blister packs. The blister pack may be a detachable communication unit for a blister pack/pill dispenser and so forth. In some embodiments, the blister pack station may include a latch for locking the blister packs via a hole on the blister packs. In some embodiments, the blister pack may comprise a raise lip and slid down and fixed to the blister pack station. The blister pack station activates on insertion of the blister pack.

The present disclosure provides a blister pack station that activates when a medication blister pack or a pill dispenser is inserted in a slot or groove of the blister pack station. The blister pack may comprise an RFID tag or a circuit for storing one or more instructions, and a chip for communicating the instructions to other devices. In some embodiments, the blister pack station is configured to receive one or more instructions stored in the blister pack or the pill dispenser. The instructions may be the instructions about the medication stored in the blister pack/pill dispenser. Further, in some embodiments, the blister pack may comprise audio/visual means comprising at least one of a luminescent coating of ink or suitable material, light emitting diodes, and so forth for providing reminders about medication based on the instructions to a user of the blister pack/pill dispenser. The user can be a patient or a caretaker.

The present disclosure provides a blister pack station capable of receiving one or more instructions from a third party such as, but not limited to, an authentic person like a doctor, pharmacist, manufacturer of medicine, a server, and so forth. For example, a doctor can put one or more instructions in the blister pack station. The blister pack station may transfer this information to a blister pack comprising a circuit or RFID tag parked in the blister pack station. The blister pack then may remind the user of the blister pack or the blister pack station according to the instructions by using at least one of the audio/visual means and mobile application on an associated computing device. Examples of the computing device may include, but are not limited to, a smart watch, a laptop, a fitness tracker, a mobile phone, a personal digital assistant, a smart TV, a desktop computer, a smart phone, a tablet computer, a smart light, and so forth.

The present disclosure provides a blister pack station configured to receive any suitable blister pack or pill dispenser or medicine pack available in the market. The blister pack or pill dispenser or medicine pack may comprise an RFID tag or a circuit and a chip for communicating information or instructions to and from other devices or authentic persons or a device in a cloud network. Further, the blister pack may be configured to update or change the instructions in real-time. In some embodiments, the blister pack station modifies the instructions stored in the blister pack/medicine pack/pill dispenser based on one or more instructions stored in the blister pack station. The blister pack station may receive instructions from a device in a cloud network.

The present disclosure provides a blister pack station configured to receive the instructions from a third party and store the instructions in a cloud network, From the cloud network any other authorized blister pack station can download the instructions. This way, the instructions from a blister pack station may be transferred and stored in the other authorized blister pack station.

The present disclosure provides a blister pack station configured to receive a blister pack/pill dispenser including an RFID tag, a circuit and a chip. The blister pack station may include one or more modules for receiving one or more instructions from a third party, reminding a user according to the instructions, communicating the instructions to other devices or cloud network, and blister pack/pill dispensers.

The one or more device may include, but are not limited to, a server, a blister pack, a computing device, and cloud network. Further, the third party may include a central server, an authorized person like doctor, pharmacist, etc. Further, the third party can store instructions in the blister pack station either indirectly via a remote server or a computing device or directly.

The present disclosure provides a blister pack station capable of storing information about medicine/tablets/pills stored in a blister pack/pill dispenser including but not limited to, batch number, date of manufacturing, dosage timing information, manufacturer information, uses, side effects, identification information and so forth.

The present disclosure provides a blister pack station comprising a feedback module or a reminder module for providing a feedback or a reminder to a user such as, but not limited to, a patient. The feedback or the reminder may comprise at least one of an audio reminder, a video reminder message, and a text message on an associated mobile device in communication with the blister pack station. In some embodiments, the blister pack station provides a visual indication based on light emitting diodes or a luminescent coating of ink or suitable material on the blister pack station or on the circuit of the blister pack. In some embodiments, the blister pack station may comprise one or more batteries for providing power to the blister pack station. The batteries may be solar operated batteries.

The present disclosure provides a blister pack station configured to program or re-program itself based on one or more events comprising such as, but not limited to, breakage of a blister pack contained in the blister pack station, a timing when the blister pack breaks or opens, a location of the blister pack/blister pack station, a time-zone, and so forth. For example, the blister pack station may adjust a timing of subsequent dosage as per the time of the dose taken recently. In some embodiments the blister pack station is configured to arrange/change the stored instructions based on a time or time zone information where the blister pack station is used. For example, if the blister pack station is initially in United States of America (USA) so initially instructions are fed into it according to the time zone of USA. Further, the bister pack station may determine where the blister pack station is for example, in which country or city in the world. If the blister pack station is used in another country like Australia then the blister pack station may change or arrange the pre-stored instructions according to the time zone of Australia. In some embodiments, the blister pack station is configured to check location of the blister pack station and/or blister pack parked in the blister pack station at regular intervals and may automatically arrange the instructions accordingly.

The present disclosure provides a blister pack station configured to communicate the information to a central server so as to check whether the medicine in a blister pack parked or stored in the blister pack station is authentic/genuine or fake.

The present disclosure provides a blister pack station comprising a chip for storing information such as, but not limited to, batch number, manufacturer, company name, expiry date, manufacturing date, uses, dosage, time for taking medicine, side-effects, and so forth of the medicine of a blister pack contained in a slot of the blister pack station. An authorized person can feed instructions comprising the information in the chip.

The present disclosure provides a blister pack station configured to remind patient about timings of taking the medicines. In some embodiments, the blister pack station also reminds the patients in case patient takes more or less dosage of a particular medicine from the blister pack.

The present disclosure provides a smart medication system comprising a blister pack station and a web means or mobile application installed on a computing device through which the medication system can remind or inform a user about medication or other information via the disclosed blister pack station. The web means or the mobile application may be in communication with the blister pack station. Further, the user may receive audio message, video message, text message, and so forth via the web means or the mobile application about the medication based on one or more instructions stored in the blister pack station.

The present disclosure provides a blister pack station comprising input means configured to receive information from a third party comprising an authentic person such a patient or a doctor. Further, the blister pack station may comprise a chip for communicating the instructions to a central server or a web-based server. In some embodiments, the blister pack station communicates the instructions or information with the central server or the web-based server when one or more events occur. The events may include, but not limited to, breakage of a blister pack stored in the blister pack station. The central server in an embodiment may check if the medicine/pills/tablets in the blister pack is genuine and authentic or not, and accordingly a feedback may be provided to a user or a patient by the blister pack station.

The present disclosure also provides a blister pack station comprising: at least one slot configured to receive at least one blister pack comprising one or more tablets; an input module configured to receive a plurality of instructions from a third party comprising at least one of an authentic person a server, a blister pack, and another blister pack station; and a chip configured to communicate the plurality of instructions to at least one of a central server, a device based in a cloud network, the blister pack, and the another blister pack station.

The present disclosure provides a blister pack station configured to connect to a mobile phone of a user like a patient. In some embodiments, the blister pack station may connect to the mobile phone via a mobile application. Further, the blister pack may provide reminders or the feedback to the patient on the mobile phone. The feedback may include at least one of an audio feedback, a video feedback, and a text feedback. The reminders may include at least one of an audio reminder, a video reminder, and a text reminder.

An embodiment of the present disclosure provides a blister pack station includes at least one slot configured to receive at least one blister pack comprising one or more tablets, wherein the blister pack station gets activated on insertion of the at least one blister pack. The blister pack station also includes an input module configured to receive a plurality of instructions about medication from at least one third party. Further, the blister pack station includes a reminder module comprising at least one of an audio module and a visual module configured to provide a reminder to a user based on the plurality of instructions. The blister pack station also includes self-programming module configured to arrange one or more instructions of the plurality of instructions based on one or more events. The blister pack station also includes a chip configured to establish a connection with at least one of at least one blister pack and the at least one third party. The chip is also configured to communicate the plurality of instructions to at least one of the at least one blister pack and the at least one third party.

Another embodiment of the present disclosure provides a blister pack station for use with at least one blister pack. The blister pack station includes at least one slot configured to receive at least one blister pack comprising a plurality of tablets. The one or more instructions may include a timing for taking the plurality of tablets, a date of manufacturing of the plurality of tablets, a batch information of the plurality of tablets, an expiry information of the plurality of tablets, and manufacturer information. The blister pack station also includes a database comprising pre-stored information about a plurality of medicines. The blister pack station also includes a reminder module configured to provide a reminder to a user about medication based on the one or more instructions. The user may receive a reminder on an associated computing device in communication with the blister pack station. Further, the blister pack station includes a self-programming module configured to arrange the one or more instructions of the medication based on one or more events. Furthermore, the blister pack station includes a chip configured to determine if the blister pack and the one or more tablets are authentic or not based on information of the blister pack and information stored in the blister pack station. The reminder module notifies the user about the authenticity based on the determination. Further, the blister pack station is retrofittable and is configured to receive or connect to any type of blister pack.

According to an aspect of the present disclosure, the chip of the blister pack station is further configured to communicate with at least one of a central server and a cloud based device when one or more events occur.

According to an aspect of the present disclosure, the blister pack station is retrofittable and is configured to receive or connect to any type of blister pack.

According to another aspect of the present disclosure, the one or more events includes at least one of a breaking of at least one of the plurality of cavity, a time at which the cavity breaks, and a time zone.

According to another aspect of the present disclosure, the third party includes at least one of an authentic person, a server, a cloud based device, a computing device, a mobile phone application, a web-based application, another blister pack station, a person, and so forth.

According to an aspect of the present disclosure, the authorized person comprising at least one of a doctor, a patient, a pharmacist, a manufacturer of the medication, and a caretaker.

According to an aspect of the present disclosure, the plurality of instructions and the one or more instructions comprising a timing for taking the one or more tablets, a date of manufacturing of the one or more tablets, a batch information of the one or more tablets, an expiry information of the one or more tablets, manufacturer information, dosage information, and so forth.

According to an aspect of the present disclosure, the reminder module sends a reminder to the user via at least one of the computing device, the audio module, and the visual module of the at least one blister pack.

According to an aspect of the present disclosure the chip is configured to: send a breakage information and information of the at least one blister pack to the server when the at least one blister pack breaks, wherein the server checks for an authenticity of the blister pack and the one or more tablets based on the breakage information and information of the blister pack, and information stored in the server. The chip is also configured to receive authenticity information of the at least one of the one or more tablets and the blister pack parked in the at least one slot of the blister pack station from the server.

According to another aspect of the present disclosure, the chip is further configured to wirelessly connect and communicate the plurality of instructions to the at least one of the server, the computing device, the device based in a cloud network, the blister pack, and the another blister pack station. The chip may wirelessly connect and communicate the plurality of instructions to the at least one of the server, the computing device, the device based in a cloud network, the blister pack, and the another blister pack station by using wireless technologies comprising Wi-Fi, Bluetooth, Near Field Communication (NFC), and so forth.

According to another aspect of the present disclosure, the blister pack station includes a database comprising pre-stored and pre-defined information about a plurality of medicines.

According to yet another aspect of the present disclosure, the at least one blister pack may include a roll of foil with an RFID chip, substrate circuits covering each component and a printed coating configured to be illuminated once a circuit is powered to indicate the compartment to open. The at least one blister pack may further include a circuit including one or more circuit connectors configured to connect to one or more connectors of the blister pack station, and receive one or more instructions from the blister pack station. Further, the at least one blister pack includes a ridge and notch to allow the blister pack station to slot and lock the at least one blister pack into a position where the one or more circuit connectors of the at least one blister pack are lined up and make contact with the one or more connectors of the blister pack station.

According to another aspect of the present disclosure, the input module is further configured to automatically fetch blister pack information from the at least blister pack.

According to yet another aspect of the present disclosure the chip is further configured to communicate the blister pack information to the server for fetching additional blister pack information about the at least one blister pack from the server.

According to another aspect of the present disclosure, a central server receives the cavity breakage information from the blister pack station via the chip.

According to another aspect of the present disclosure, the blister pack station is configured to receive the breakage information from the blister pack and transfer the breakage information to the central server via the chip.

According to another aspect of the present disclosure, the blister pack comprising a circuit configured to receive one or more instructions from the blister pack station.

According to another aspect of the present disclosure, the blister pack further comprises a chip for storing the instructions and information about the medicine, manufacturers, dosage, diseases, and batch information.

According to yet another aspect of the present disclosure, the reminder module is configured to inform the patient if the medicine is not authentic based on one or more communication with the central server received when the cavity breaks.

According to yet another aspect of the present disclosure, the blister pack station may further include a display module (not shown) to display instructions and information. In some embodiments, the display module may display reminders, instructions, notifications, and information etc. about the medicines, users, and so forth.

The systems and methods disclosed in the present disclosure are widely applicable to the field of patient management, medicines, and hospitals.

Other and further aspects and features of the disclosure will be evident from reading the following detailed description of the embodiments, which are intended to illustrate, not limit, the present disclosure.

BRIEF DESCRIPTION OF THE DRAWINGS

The illustrated embodiments of the disclosed subject matter will be best understood by reference to the drawings, wherein like parts are designated by like numerals throughout. The following description is intended only by way of example, and simply illustrates certain selected embodiments of devices, systems, and processes that are consistent with the disclosed subject matter as claimed herein.

DETAILED DESCRIPTION

Figure 1:
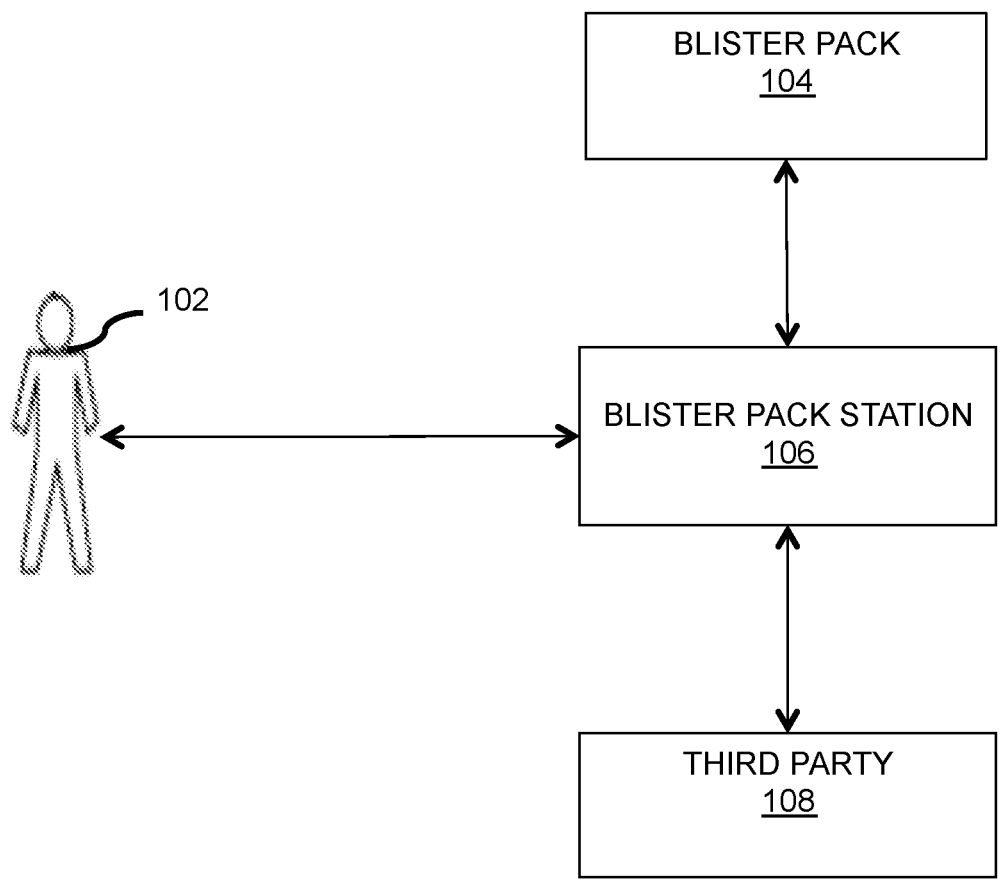
FIG. 1 is a schematic diagram illustrating an exemplary environment, where various embodiments of the present disclosure may function.

The following detailed description is made with reference to the figures. Exemplary embodiments are described to illustrate the disclosure, not to limit its scope, which is defined by the claims. Those of ordinary skill in the art will recognize a number of equivalent variations in the description that follows.

The functional units described in this specification have been labeled as devices. A device may be implemented in programmable hardware devices such as processors, digital signal processors, central processing units, field programmable gate arrays, programmable array logic, programmable logic devices, cloud processing systems, or the like. The devices may also be implemented in software for execution by various types of processors. An identified device may include executable code and may, for instance, comprise one or more physical or logical blocks of computer instructions, which may, for instance, be organized as an object, procedure, function, or other construct. Nevertheless, the executable of an identified device need not be physically located together, but may comprise disparate instructions stored in different locations which, when joined logically together, comprise the device and achieve the stated purpose of the device.

Indeed, an executable code of a device or module could be a single instruction, or many instructions, and may even be distributed over several different code segments, among different applications, and across several memory devices. Similarly, operational data may be identified and illustrated herein within the device, and may be embodied in any suitable form and organized within any suitable type of data structure. The operational data may be collected as a single data set, or may be distributed over different locations including over different storage devices, and may exist, at least partially, as electronic signals on a system or network.

Reference throughout this specification to "a select embodiment," "one embodiment," or "an embodiment" means that a particular feature, structure, or characteristic described in connection with the embodiment is included in at least one embodiment of the disclosed subject matter. Thus, appearances of the phrases "a select embodiment," "in one embodiment," or "in an embodiment" in various places throughout this specification are not necessarily referring to the same embodiment.

Furthermore, the described features, structures, or characteristics may be combined in any suitable manner in one or more embodiments. In the following description, numerous specific details are provided, to provide a thorough understanding of embodiments of the disclosed subject matter. One skilled in the relevant art will recognize, however, that the disclosed subject matter can be practiced without one or more of the specific details, or with other methods, components, materials, etc. In other instances, well-known structures, materials, or operations are not shown or described in detail to avoid obscuring aspects of the disclosed subject matter.

The blister pack station includes a circuit that may include a software, hardware, firmware, or combination of these.

In accordance with the exemplary embodiments, the disclosed computer programs or modules can be executed in many exemplary ways, such as an application that is resident in the memory of a device or as a hosted application that is being executed on a server and communicating with the device application or browser via a number of standard protocols, such as TCP/IP, HTTP, XML, SOAP, REST, JSON and other sufficient protocols. The disclosed computer programs can be written in exemplary programming languages that execute from memory on the device or from a hosted server, such as BASIC, COBOL, C, C++, Java, Pascal, or scripting languages such as JavaScript, Python, Ruby, PHP, Perl or other sufficient programming languages.

Some of the disclosed embodiments include or otherwise involve data transfer over a network, such as communicating various inputs or files over the network. The network may include, for example, one or more of the Internet, Wide Area Networks (WANs), Local Area Networks (LANs), analog or digital wired and wireless telephone networks (e.g., a PSTN, Integrated Services Digital Network (ISDN), a cellular network, and Digital Subscriber Line (xDSL)), radio, television, cable, satellite, and/or any other delivery or tunneling mechanism for carrying data. The network may include multiple networks or sub networks, each of which may include, for example, a wired or wireless data pathway. The network may include a circuit-switched voice network, a packet-switched data network, or any other network able to carry electronic communications. For example, the network may include networks based on the Internet protocol (IP) or asynchronous transfer mode (ATM), and may support voice using, for example, VoIP, Voice-over-ATM, or other comparable protocols used for voice data communications. In one implementation, the network includes a cellular telephone network configured to enable exchange of text or SMS messages.

Examples of the network include, but are not limited to, a personal area network (PAN), a storage area network (SAN), a home area network (HAN), a campus area network (CAN), a local area network (LAN), a wide area network (WAN), a metropolitan area network (MAN), a virtual private network (VPN), an enterprise private network (EPN), Internet, a global area network (GAN), and so forth.

The main objective of the present disclosure is to provide a blister pack station, controller, server, application, software/hardware application, and/or a circuit to use with any suitable blister pack/pill dispenser/tablet package, and the like. Any suitable blister pack with a circuit or/and RFID tag and light emitting diodes and/or luminescent coating may be inserted in the blister pack station for activating the blister pack station. The blister pack may comprise a lip along an edge of the blister pack. In small embodiments, the blister pack may comprise a small hole alongside the lip for a latch of the blister pack station. Further, the blister pack may comprise a chip such as, but not limited to, a Read Only Memory (ROM) chip in the case of a manufacturers production line or an Erasable-Programmable Read Only Memory (EPROM or FROM) chip where a local pharmacist or doctor may load or seal the blister pack and may need to enter instructions or details onto the chip at the time of packing the blister pack.

FIG. 1 is a schematic diagram illustrating an exemplary environment 100, where various embodiments of the present disclosure may function. As shown, the environment 100 includes a user 102, a blister pack 104, a blister pack station 106, and a third party 108. The user 102 may be a patient or a caretaker of the patient.

The blister pack 104 may be a pack for storing or containing medicines/tablets/pills. The blister pack 104 may include a number of cavities for storing the medicine, pills, capsules, or tablets. The blister pack 104 may pack the medicines, pills, capsules, or tablets in a secure manner. In some embodiments, the blister pack 104 may store more than one type of medicine in the cavities. Further, the blister pack 104 may have a circuit embossed in a cover of the blister pack 104. In some embodiments, the circuit may include a visual means for indicating or reminding the patient about time or dosage of the medicine. In some embodiments, the circuit includes LEDs and batteries for providing visual reminders to the patient. Further, the LEDs may light in different colors or patterns for providing different type of reminders to the patient. In some embodiments, the visual means may comprise a luminescent coating of suitable material that may light up to remind the user 102 about the medication.

In some embodiments, the blister pack 104 may include a roll of foil with an RFID chip, substrate circuits covering each component and a printed coating configured to be illuminated once a circuit is powered to indicate the compartment to open. The blister pack 104 may also include the circuit including one or more circuit connectors configured to connect to one or more connectors of the blister pack station, and receive one or more instructions from the blister pack station. In some embodiments, the blister pack 104 may include a ridge and notch to allow the blister pack station to slot and lock the at least one blister pack into a position where the one or more circuit connectors of the at least one blister pack are lined up and make contact with the one or more connectors of the blister pack station. In some embodiments, a straight side of the blister pack 104 may be modified to include a ridge and notch to allow the blister pack station to slot and lock the at least one blister pack into a position where the one or more circuit connectors of the at least one blister pack are lined up and make contact with the one or more connectors of the blister pack station.

The blister pack station 106 may include at least one slot for receiving the blister pack 104 containing one or more tablets. In some embodiments, the blister pack station 106 comprises a latch for locking the blister pack 104 via a hole of the blister pack 104. The blister pack station 106 is retrofittable and may receive or connect to any type of blister pack including all types of existing blister packs. The blister pack station 106 may get activated on insertion of the at least one blister pack 104.

The blister pack station 106 establish a connection with at least one of the at least one blister pack, such as the blister pack 104, and the at least one third party 108. The blister pack station 106 then may communicate the plurality of instructions to at least one of the at least one blister pack 104 and the at least one third party 108.

In some embodiments, the blister pack station 106 may establish a connection with the blister pack 104 (may also be referred as a pill dispenser without change in its meaning) wirelessly and may get activated on successful establishment of the connection. The bister pack station 106 is configured to fetch blister pack information from the blister pack 104. In some embodiments, the blister pack station 106 may establish a connection with the blister pack 104 (may also be referred as a pill dispenser without Change in its meaning) wirelessly by using suitable wireless technologies like NFC, Wi-Fi, Bluetooth, and the like.

The blister pack station 106 is configured to receive one or more instructions from the third party 108. The third party may include such as, but not limited to, an authentic person like a doctor, pharmacist, and a manufacturer of medicine, a server, a cloud based device, a computing device, a mobile phone application, a web-based application, another blister pack station, a person, and so forth. For example, a doctor can put one or more instructions in the blister pack station 106. The blister pack station 106 may transfer this information to the blister pack 104 comprising the circuit or RFID tag parked in the blister pack station 106. The blister pack 104 then may remind the user 102 of the blister pack 104 or the blister pack station 106 according to the instructions by using at least one of the audio/visual means and/or mobile application on an associated computing device of the user 102.

In some embodiments, the blister pack station 106 may send a breakage information of the at least one blister pack to the server when the at least one blister pack breaks. Further, the blister pack station 106 may receive authenticity information of the one or more tablets stored in the at least one blister pack parked in the at least one slot of the blister pack station.

In some embodiments, the blister pack station 106 may receive instructions from a device in a cloud network. The instructions may include a timing for taking the one or more tablets, a date of manufacturing of the one or more tablets, a batch information of the one or more tablets, an expiry information of the one or more tablets, manufacturer information, and dosage information. From the cloud network any other authorized blister pack station can download the instructions. This way, the instructions from the blister pack station 106 may be transferred and stored in the other authorized blister pack station. Further, the blister pack station 106 may communicate the instructions to other devices or cloud network, and blister pack/pill dispensers. The one or more device may include, but are not limited to, a server, a blister pack, a computing device, and cloud network.

Further, the third party 108 may include a central server. Further, the third party 108 can store instructions in the blister pack station 106 either indirectly via a remote server or a computing device or directly.

In some embodiments, the blister pack station 106 is further configured to wirelessly connect and communicate the plurality of instructions to the at least one of the server, the computing device, the device based in a cloud network, the blister pack, and the another blister pack station. Further, the blister pack station 106 may include a database comprising pre-stored information about a plurality of medicines.

Further, the blister pack station 106 is further configured to automatically fetch blister pack information from the at least blister pack. The blister pack station 106 may communicate the blister pack information to the server for fetching additional blister pack information about the at least one blister pack from the server.

Examples of the authorized person may include, but are not limited to, at least one of a doctor, a patient, the user 102, a pharmacist, a manufacturer of the medication, and a caretaker.

The blister pack station 106 may store instruction or information about medicine/tablets/pills stored in a blister pack/pill dispenser including but not limited to, batch number, date of manufacturing, dosage timing information, manufacturer information, uses, side effects, identification information and so forth. Further, the blister pack station 106 is configured to program or re-program itself based on one or more events comprising such as, but not limited to, breakage of the blister pack 104 contained in the blister pack station 106, a timing when the blister pack 104 breaks or opens, a location of the blister pack 104/blister pack station 106, a time-zone, and so forth. For example, the blister pack station 106 may adjust a timing of subsequent dosage as per the time of the dose taken recently. In some embodiments the blister pack station 106 is configured to arrange/change the stored instructions based on a time or time zone information where the blister pack station 106 is used. For example, if the blister pack station 106 is initially in United States of America (USA) so initially instructions are fed into it according to the time zone of USA. Further, the bister pack station 106 may determine where the blister pack station 106 is for example, in which country or city in the world. If the blister pack station 106 is used in another country like Australia then the blister pack station 106 may Change or arrange the pre-stored instructions according to the time zone of Australia. In some embodiments, the blister pack station 106 is configured to check a location of the blister pack station 106 and/or blister pack 104 parked or inserted in the blister pack station 106 at regular intervals and may automatically arrange the instructions accordingly.

The third party 108 may be an authorized person comprising any person authorized to feed or store instructions in the blister pack station 106. Examples of the authorized person may include, but are not limited to a doctor, manufacturer of medicine, a caretaker, a pharmacist, a patient, and so forth. The third party may also include a server, a computing device, another blister pack station, and so forth. The computing device can be any suitable device such as, but not limited to, a smart phone, a smart watch, a fitness tracker, a desktop computer, a laptop computer, a tablet computer, a personal digital assistant, a smart television, and so forth, capable of communicating with the blister pack station 106. In some embodiments, the third party 108 communicates with the blister pack station 106 via one or more mobile applications. In some embodiments, the third party 108 provides a plurality of instructions comprising a timing for taking the tablets, a date of manufacturing of the tablets, a batch information of the tablets, an expiry information of the tablets, manufacturer information, and so forth.

The server or central server may be a remotely located centralized server comprising information about the medicines stored in the blister pack 104. The information may include, but are not limited to, batch number, date of expiry, date of manufacturing, dosage information, manufacturer of the medicine, side effects, usage, identification, and so forth.

In some embodiments, the blister pack 104 may comprise an MID tag, a circuit and/or a chip. The blister pack 104 may also comprise the circuit comprising one or more modules. The circuit may comprise at least one battery. The blister pack 104 may comprise one or more light emitting diodes (LEDs) and/or a luminescent material coating for reminding the user 102 about a time of taking the medicine. The blister pack 104 may be a plastic blister pack having dimensions of 2 mm×2 mm×50 mm and raised lip that may allow the blister pack 104 to slid down and fix to the blister pack station 106. In some embodiments, the blister pack 104 may have a hole alongside the lip and the blister pack station 106 may include a latch for locking the pack via the hole into the place and align all the circuit connections to then activate and light up the LEDs or luminescent coating of the blister pack 104 based on the instructions.

Further, the blister pack 104 may receive one or more instructions from the authorized person and/or the server directly or indirectly over a network (not shown). In some embodiments, the blister pack 104 may be configured to receive instructions and store instructions in a cloud network. Further, the blister pack 104 may be configured to automatically update or change the instructions in real-time.

The blister pack 104 may store the one or more instructions in the chip. The LEDs may light up based on the instructions. Further, the blister pack 104 may be configured to arrange or modify the stored information and instructions based on one or more events for example, but not limited to, a time zone, a time when the pack breaks, and so forth.

The blister pack station 106 may include at least one of an audio module and a visual module configured to provide a reminder to the user 102 (hereinafter, the user 102 may be referred as patient 102) based on the plurality of instructions.

The blister pack station 106 may be configured to arrange one or more instructions of the plurality of instructions based on one or more events. In some embodiments, the blister pack station 106 sends a reminder to the user 102 via at least one of the computing device of the user 102, the audio module, and the visual module of the blister pack 104. The reminders may be provided in form of an audio reminder, visual reminder, text reminder, a notification, a haptic feedback, and so forth.

Further, the blister pack station 106 may be configured to connect to a mobile phone of the user 102 like a patient. In some embodiments, the blister pack station 106 may connect to the mobile phone via a mobile application. In an example, the blister pack station 106 may provide reminders or the feedback to the patient 102 on the mobile phone. The feedback may include at least one of an audio feedback, a video feedback, and a text feedback. The reminders may include at least one of an audio reminder, a video reminder, and a text reminder.

Further, the blister pack station 106 may communicate with the central server when one or more events occur. The events may include, but not limited to, breakage of the blister pack 104. The central server in an embodiments may check if the medicine is genuine and authentic or not, and accordingly a feedback may be provided to the patient by the blister pack station 106.

Figure 2:
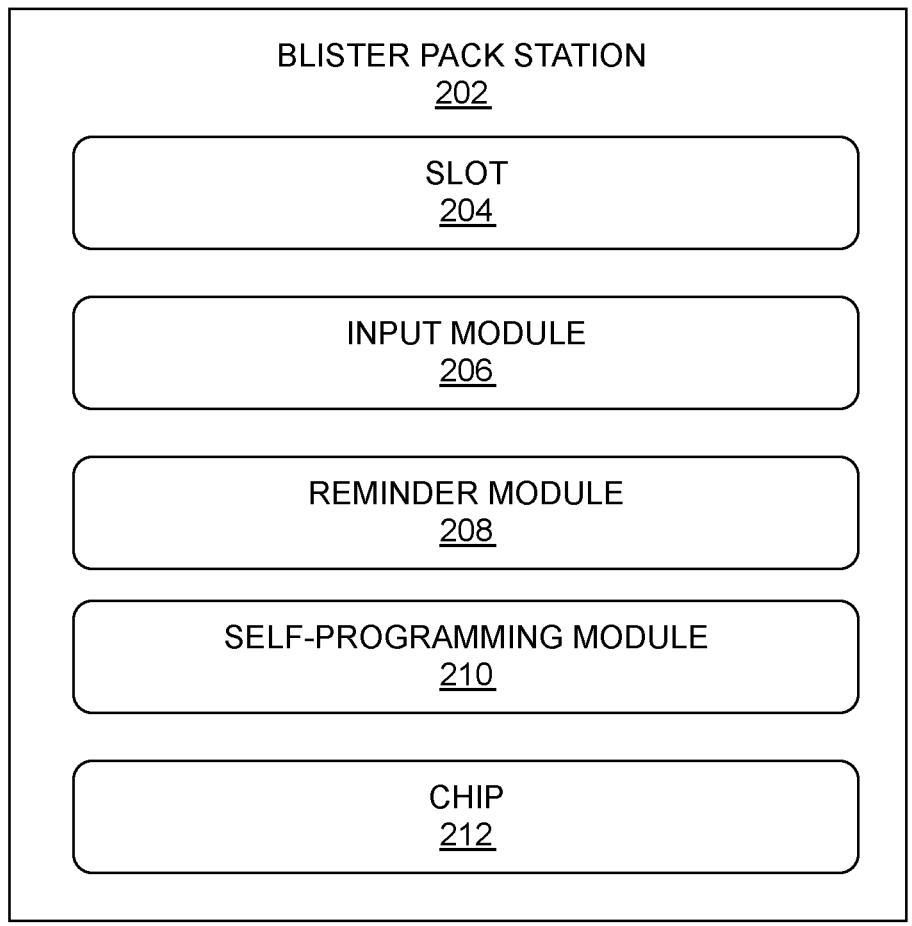
FIG. 2 is a block diagram illustrating various system elements of an exemplary blister pack station, in accordance with an embodiment of the present disclosure.

FIG. 2 is a block diagram 200 illustrating various system elements of an exemplary blister pack station 202, in accordance with an embodiment of the present disclosure. As shown, the blister pack station 202 primarily includes at least one slot 204, an input module 206, a reminder module 208, a self-programming module 210, and a chip 212. As discussed with reference to FIG. 1, the blister pack station 202 may receive at least one blister pack such as the blister pack 104 in the at least one slot 204. The blister pack 104 may slide down in the slot or may lock into a, latch of the blister pack station 202 via a small hole on an edge of the blister pack 104. When the blister pack 104 is properly parked in the at least one slot 204, a connection between the blister pack station 202 and the blister pack establishes. In some embodiments, the blister pack station 202 establishes the connection with the blister pack 104 wirelessly and may not require the blister pack 104 to be parked into the at least one slot 204. The bister pack 104 may include the medication such as, medicine, tablets, capsules, or pills.

The blister pack station 202 may receive one or more instructions about the medication from the third party 108 via the input module 206. The input module 206 is configured to receive and store one or more instructions from the third party 108, The one or more instructions may include such as, but not limited to, a timing for taking the plurality of tablets, a date of manufacturing of the plurality of tablets, a batch information of the plurality of tablets, an expiry information of the plurality of tablets, and manufacturer information. The third party 108 can be an authorized person, a server, a cloud-based device, a computing device, a mobile phone application, a web-based application, another blister pack station, a person, and so forth. The authorized person may be the user 102, a doctor, a patient, a pharmacist, a caretaker, a manufacturer of the medication, and so forth.

The reminder module 208 is configured to provide a reminder or feedback to the user 102 based on the one or more instructions. The reminder module 208 may include at least one of an audio module for providing an audio reminder (or feedback) to the user 102 and a visual module for providing a video reminder (or feedback) to the user 102 based on the one or more instructions. In some embodiments, the user 102 receives a reminder on an associated computing device in communication with the blister pack station 202. Further, the reminder module 208 sends a reminder to the user 102 via at least one of a computing device, an audio module, and a visual module of the blister pack. For example, an audio message may be played on the computing device of the user 102 for reminding about a timing of taking the medicine. The visual module may include one or more light emitting diodes (LEDs) and/or luminescent coating or suitable ink or material that may light up to provide a reminder. The LEDs may light up based on the instructions. Further, the LEDs may light in different colors or patterns for providing different type of reminders to the patient. The audio module may include a speaker. The audio and visual modules may provide a feedback to the patient or the user 102. In some embodiments, the patient receives a reminder on the mobile phone in communication with the blister pack station 202. Further, the reminder module 208 is configured to inform the patient if the medicine is not authentic based on one or more communication with the central server received when the cavity breaks. The feedback or the reminder may include at least one of an audio reminder, a video/visual reminder message, and a text message on the associate computing device in communication with the blister pack station 202. In some embodiments, the blister pack station 202 may provide a visual indication based on light emitting diodes on the circuit of the blister pack. Further, the blister pack 104 may include one or more batteries for providing power to the LEDs. In some embodiments, the batteries may be solar operated batteries. The at least one battery may provide power to the LEDs. The battery may be a solar battery.

The self-programming module 210 is configured to arrange one or more instructions of the medication based on one or more events. The one or more events may include such as, but not limited to, a breaking of at least one of the plurality of cavity, a time at which the cavity breaks, and a time zone. The self-programming module 210 may be configured to automatically update or change the instructions in real-time.

Further, the blister pack station 202 may include one or more batteries for providing power to the chip. In some embodiments, the batteries may be solar operated batteries. The at least one battery may provide power to the LEDs of the blister pack station 202. The battery may be a solar battery and/or a rechargeable battery.

The chip 212 is configured to establish a connection with at least one of the at least one blister pack 104 and the at least one third party 108. The chip 212 is also configured to communicate the plurality of instructions to at least one of the at least one blister pack 104 and the at least one third party 108. The chip 212 may also be configured to communicate with at least one of a central server and a cloud-based device when one or more events occur. In some embodiments, the chip 212 is further configured to send breakage information of the blister pack 104 to the central server when the blister pack 104 breaks and receive authenticity information of the one or more tablets stored in the blister pack 104 in connection with or parked in the at least one slot of the blister pack station from the central server. The reminder module 208 may remind or notify the user 102 about an authenticity of the medication (i.e. the one or more tablets stored in the blister pack 104) based on the received authenticity information. The chip 212 can be such as, but not limited to, a ROM chip or an EPROM chip.

The chip 212 is further configured to wirelessly connect and communicate the plurality of instructions to the at least one of the server, the computing device, the device based in a cloud network, the blister pack 104, and the another blister pack station.

In some embodiments, the chip 212 is configured to determine if the blister pack and the one or more tablets are authentic or not based on information of the blister pack 104 and information stored in the blister pack station 202. The reminder module 208 may notify the user about the authenticity based on the determination.

In some embodiments, the chip 212 is configured to send a breakage information and information of the at least one blister pack 104 to the server when the at least one blister pack 104 breaks. The server may check for an authenticity of the blister pack 104 and the one or more tablets based on the breakage information and information of the blister pack 104, and information stored in the server. The chip 212 is configured to receive authenticity information of the at least one of the one or more tablets and the blister pack 104 parked in the at least one slot of the blister pack station 106 from the server. The authenticity information may indicate if the blister pack and/or the tablets are authentic or not. The reminder module 208 may provide a reminder or feedback to the user 102 based on the authenticity information.

Though not shown, but the blister pack station 202 may also include a database comprising pre-stored information about a plurality of medicines. The blister pack station 202 is configured to automatically update the database. In some embodiments, the blister pack station 202 automatically updates the database based on information and/or instructions received from the server, authorized person, blister pack 104, and so forth.

In some embodiments, the chip 212 is configured to communicate the plurality of instructions to at least one of a central server, a device based in a cloud network, the blister pack 104, and the another blister pack station.

The chip 212 may store one or more instructions or information about the stored medicine/pills/tablets, manufacturers, dosage, diseases, and batch information. In some embodiments, the instructions comprising a timing for taking the tablets, a date of manufacturing of the tablets, a batch information of the tablets, an expiry information of the tablets, manufacturer information, and so forth.

The chip 212 may be configured to communicate with one or more device such as, the server and the computing device for receiving or sending the instructions. Further, the computing device may include a mobile phone, a mobile phone application, a personal digital assistant, a smart watch, and so forth. Further, the chip 212 may send the cavity breakage information to the central server. Further, the chip 212 may receive one or more instructions from the authorized person and/or the server directly or indirectly over a network (not shown).

In some embodiments, the input module 206 is further configured to automatically fetch blister pack information from the at least blister pack 104.

The blister pack station 202 may further include a display module (not shown) to display instructions and information. In some embodiments, the display module may display reminders, instructions, notifications, and information etc. about the medicines, users, and so forth.

Figure 3:
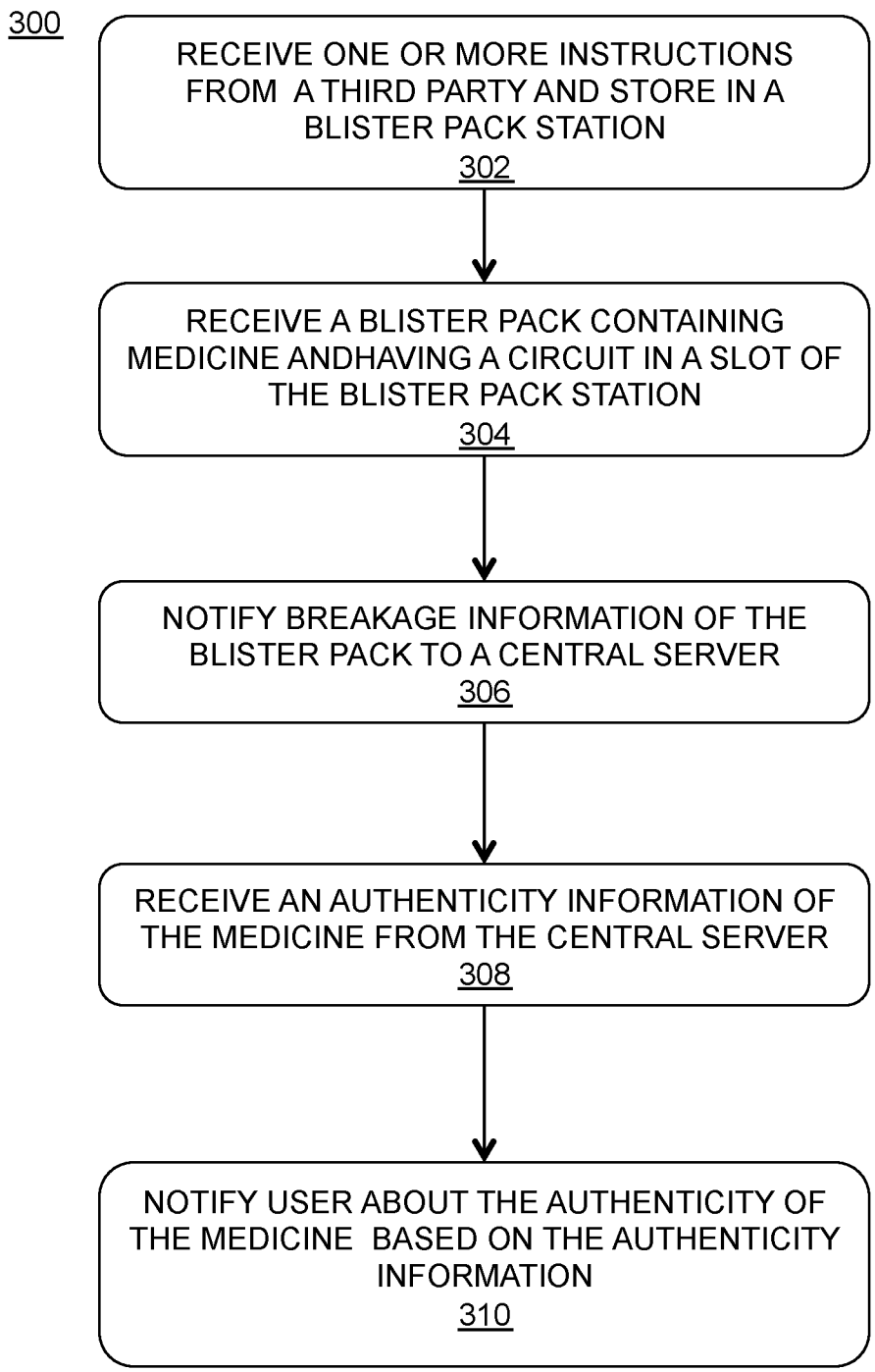
FIG. 3 is a flowchart diagram illustrating a method for using the exemplary blister pack station of FIG. 2, in accordance with an embodiment of the present disclosure.

FIG. 3 is a flowchart diagram illustrating a method 300 for using the exemplary blister pack station 202 of FIG. 2, in accordance with an embodiment of the present disclosure.

At step 302, the blister pack station 202 may receive one or more instructions from a third party such as, but not limited to a pharmacist and store in the blister pack station 202 or in a cloud based server or device. Then at step 304, the a blister pack such as the blister pack 104 as discussed with reference to FIG. 1 may be inserted into the at least one slot 204 of the blister pack station 202, this activates the blister pack station 202. Then at step 306, when the blister pack 104 breaks or is opened, then a breakage information of the blister pack 104 is received from the blister pack and sent to a central server or a cloud based device. Then at step 308, an authenticity information of medicine contained in the blister pack is received from the central server or the cloud based device. The central server may check whether the medicine is fake or original and inform the blister pack station 202 accordingly. Thereafter, at step 310, the blister pack station 202 notifies the user 102 about an authenticity of the medicine in the blister pack 104 based on the authenticity information received from the central server. The blister pack station 202 may notify using audio/visual means to the user 102.

The disclosed blister pack station has slot for receiving a blister pack having cavities to keep the tablets and each of the cavities have visual means to inform the patient or the user about medication timing reminder.

The disclosed blister pack station may store pre-fed or pre-defined instructions and information about a plurality of medicines.

The disclosed blister pack station is configured to communicate with other devices for exchanging information and instructions.

The disclosed blister pack station comprises a chip for storing the instructions and information about the medication.

The disclosed blister pack station is configured to notify the user of the blister pack or the blister pack station about authenticity of medicine contained in the blister pack.

The disclosed blister pack station is configured to remind the user using audio/visual means based on the pre-stored instructions. Hence, the user may not have to remember the instructions all the time.

The disclosed blister pack station can be used with any suitable blister pack.

The disclosed blister pack station may be configured to transfer instructions to other blister pack stations over a network.

The disclosed blister pack station may transfer instructions to a blister pack having a circuit and/or an RFID tag when the blister pack is inserted in the blister pack station.

The disclosed blister pack station may receive one or more instructions from a blister pack having a circuit and/or an RFID tag when the blister pack is inserted in the blister pack station.

The server may store instructions and/or information about a plurality of medicines. In some embodiments; the server may update the instructions and the information over a period of time automatically. The server may update the instructions and the information over a period of time based on communication with the blister pack station 106.

The disclosed blister pack station is a universal platform that may be used with the blister packs available in the market by doing minor modification in the existing blister packs. For example, existing blister packs may adapt to become smart enabled blister packs by remolding the leading edge of a blister pack and thickening the plastic to form an example 2 mm×2 mm×50 mm raised lip may allow the plastic blister pack to be slid down and fixed to the disclosed blister pack station. Further, a hole may be present in the blister pack alongside the lip then a latch on the blister pack station may lock the blister pack into the place and align all the circuit connections to then activate and light up the LEDs or luminescent coating.

An embodiment of the present disclosure provides a blister pack station including: a slot configured to receive at least one blister pack comprising a plurality of tablets; an input module configured to receive and store one or more instructions from at least one third party, wherein the instructions comprising a timing for taking the tablets, a date of manufacturing of the tablets, a batch information of the tablets, an expiry information of the tablets, and manufacturer information; a reminder module configured to provide a reminder to a user about medication based on the one or more instructions, wherein the user receives a reminder on a computing device in communication with the blister pack station; or more instruction about the medication from the at least one third party; a self-programming module configured to arrange the one or more instructions of the medication based on one or more events; and a chip configured to: send a breakage information of the blister pack to a server when the blister pack breaks for checking an authenticity of the tablets contained in the blister pack; and receive authenticity information of the tablets. The reminder module notifies the user based on the authenticity information of the tablets.

Another embodiment of the present disclosure provides a blister pack station comprising: at least one slot configured to receive at least one blister pack comprising one or more tablets; an input module configured to receive a plurality of instructions from a third party comprising at least one of an authentic person a server, a blister pack, and another blister pack station; and a chip configured to communicate the plurality of instructions to at least one of a central server, a device based in a cloud network, the blister pack, and the another blister pack station.

According to an aspect of the present disclosure, the chip of the blister pack station is further configured to communicate with at least one of a central server and a cloud based device when one or more events occur.

According to another aspect of the present disclosure, the one or more events includes at least one of a breaking of at least one of the plurality of cavity, a time at which the cavity breaks, and a time zone.

According to another aspect of the present disclosure, the third party includes at least one of an authentic person, a server, a cloud based device, a computing device, a mobile phone application, a web-based application, another blister pack station, a person, and so forth.

According to an aspect of the present disclosure, the authorized person comprising at least one of a doctor, a patient, a pharmacist, a manufacturer of the medication, and a caretaker.

According to an aspect of the present disclosure, the plurality of instructions and the one or more instructions comprising a timing for taking the one or more tablets, a date of manufacturing of the one or more tablets, a batch information of the one or more tablets, an expiry information of the one or more tablets, manufacturer information, dosage information, and so forth.

According to an aspect of the present disclosure, the reminder module sends a reminder to the user via at least one of the computing device, the audio module, and the visual module of the at least one blister pack.

According to an aspect of the present disclosure the chip is configured to: send a breakage information of the blister pack to the server when the at least one blister pack breaks; and receive authenticity information of the one or more tablets stored in the at least one blister pack parked in the at least one slot of the blister pack station.

According to another aspect of the present disclosure, the blister pack comprising a circuit configured to receive one or more instructions from the blister pack station.

According to another aspect of the present disclosure, the blister pack further comprises a chip for storing the instructions and information about the medicine, manufacturers, dosage, diseases, and batch information.

According to yet another aspect of the present disclosure, the reminder module is configured to inform the patient if the medicine is not authentic based on one or more communication with the central server received when the cavity breaks.

According to another aspect of the present disclosure, the input module is further configured to automatically fetch blister pack information from the at least blister pack.

According to yet another aspect of the present disclosure the chip is further configured to communicate the blister pack information to the server for fetching additional blister pack information about the at least one blister pack from the server.

According to another aspect of the present disclosure, a central server receives the cavity breakage information from the blister pack station via the chip.

According to another aspect of the present disclosure, the blister pack station is configured to receive the breakage information from the blister pack and transfer the breakage information to the central server via the chip.

The systems and methods disclosed in the present disclosure are widely applicable to the field of patient management, medicines, and hospitals.

The disclosed blister pack station is capable of receiving and/or storing one or more instructions or information from a third party. The third party can be an authorized person, a server, a computing device like a mobile phone, a smart watch, a by brid watch, a laptop, a tablet computer, a desktop computer, a personal digital assistant, a smart television, and so forth. In some embodiments, the blister pack station may receive the instruction about the medication like, but not limited to, a timing for taking the tablets, a date of manufacturing of the tablets, a batch information of the tablets, an expiry information of the tablets, manufacturer information, and so forth.

According to an aspect of the present disclosure, the chip is further configured to wirelessly connect and communicate the plurality of instructions to the at least one of the server, the computing device, the device based in a cloud network, the blister pack, and the another blister pack station.

According to another aspect of the present disclosure, the blister pack station includes a database comprising pre-stored and pre-defined information about a plurality of medicines.

According to yet another aspect of the present disclosure, the at least one blister pack may include a roll of foil with an RFID chip, substrate circuits covering each component and a printed coating configured to be illuminated once a circuit is powered to indicate the compartment to open. The at least one blister pack may further include a circuit including one or more circuit connectors configured to connect to one or more connectors of the blister pack station, and receive one or more instructions from the blister pack station. Further, the at least one blister pack includes a ridge and notch to allow the blister pack station to slot and lock the at least one blister pack into a position where the one or more circuit connectors of the at least one blister pack are lined up and make contact with the one or more connectors of the blister pack station.

Further, the disclosed blister pack station is configured to receive a blister pack or a pill dispenser. The blister pack can be inserted in a slot of the blister pack station for activating the blister pack station. In some embodiments, the blister pack station may receive instructions from a third party and may communicate the stored instructions to the blister pack/pill dispenser. Further, the blister pack station may be configured to transfer these instructions or information to other devices like mobile phones, servers, other blister pack, and the like.

In some embodiments, the disclosed blister pack station is configured to fetch blister pack information from a blister pack via wireless or wired means. The blister pack station then may send this information to the third party device like a server (may also be referred as a central server) for fetching additional blister pack information from the server. The blister pack information and the additional blister pack information may be stored in a database of the blister pack station.

Further, the disclosed blister pack station is retrofittable and may be configured to receive or connect to any existing blister pack. The disclosed blister pack station may connect with the blister pack or the server via a wireless connection like Bluetooth, near field communication (NFC), and so forth. The blister pack contains a number of tablets.

In some embodiments, the disclosed blister pack station communicates with the central server to find information about the blister pack that is in communication with the blister pack station or is parked in the slot of the blister pack station.

The disclosed blister pack station may store pre-defined information about a plurality of medicines. When a blister pack is connected to or brought near or put into the slot of the blister pack station, then the blister pack station may automatically fetch the blister pack information Based on the blister pack information, the blister pack station may determine additional blister pack information from the pre-defined information. The pre-defined information may include information like, color, shape, composition, uses, dosage, side effects of the medicines, and so forth.

The disclosed blister pack station is capable of storing one or more instructions or information received from a third party comprising an authentic person. Further, the blister pack station may be configured to arrange or modify the stored information and instructions based on one or more events for example, but not limited to, a time zone, a time when a stored blister pack breaks or opens, and so forth.

The disclosed blister pack station further comprising a display module to display instructions and information.

The disclosed blister pack station (hereinafter, may also be referred as a blister pack controlling station) configured to receive one or more instructions from at least one authorized third party. Further, the blister pack controlling station is configured to transfer or communicate the one or more instructions to another devices comprising blister packs, other blister pack controlling stations, servers, mobile devices, smart watches, laptops, tablet computers, and so forth. Further, the blister pack controlling station can receive any suitable blister pack. In an example, the blister pack may be a plastic blister pack having dimensions of 2 mm×2 mm×50 mm and raised lip that may allow the blister pack to slid down and fix to the blister pack controlling station. In some embodiments, the blister packs may have a hole alongside the lip and the blister pack controlling station may include a latch for locking the pack via the hole into the place and align all the circuit connections to then activate and light up the LEDs or luminescent coating of the blister pack.

The disclosed blister pack station is configured to communicate with a third party for exchanging information and instruction about medication and blister packs. The blister pack may be a detachable communication unit for a blister pack/pill dispenser and so forth. In some embodiments, the blister pack station may include a latch for locking the blister packs via a hole on the blister packs. In some embodiments, the blister pack may comprise a raise lip and slid down and fixed to the blister pack station. The blister pack station activates on insertion of the blister pack.

The disclosed blister pack station gets activated when a medication blister pack or a pill dispenser is inserted in a slot or groove of the blister pack station. The blister pack may comprise an RFID tag or a circuit for storing one or more instructions, and a chip for communicating the instructions to other devices. In some embodiments, the blister pack station is configured to receive one or more instructions stored in the blister pack or the pill dispenser. The instructions may be the instructions about the medication stored in the blister pack/pill dispenser. Further, in some embodiments, the blister pack may comprise audio/visual means comprising at least one of a luminescent coating of ink or suitable material, light emitting diodes, and so forth for providing reminders about medication based on the instructions to a user of the blister pack/pill dispenser. The user can be a patient or a caretaker.

The disclosed blister pack station is configured for receiving one or more instructions from a third party such as, but not limited to, an authentic person like a, doctor, pharmacist, manufacturer of medicine, a server, and so forth. For example, a doctor can put one or more instructions in the blister pack station. The blister pack station may transfer this information to a blister pack comprising a circuit or RFID tag parked in the blister pack station. The blister pack then may remind the user of the blister pack or the blister pack station according to the instructions by using at least one of the audio/visual means and mobile application on an associated computing device. Examples of the computing device may include, but are not limited to, a smart watch, a laptop, a fitness tracker, a mobile phone, a personal digital assistant, a smart TV, a desktop computer, a smart phone, a tablet computer, a smart light, and so forth.

The disclosed blister pack station is configured to receive any suitable blister pack or pill dispenser or medicine pack available in the market. The blister pack or pill dispenser or medicine pack may comprise an RFID tag or a circuit and a chip for communicating information or instructions to and from other devices or authentic persons or a device in a cloud network. Further, the blister pack may be configured to update or change the instructions in real-time. In some embodiments, the blister pack station modifies the instructions stored in the blister pack/medicine pack/pill dispenser based on one or more instructions stored in the blister pack station. The blister pack station may receive instructions from a device in a cloud network.

The disclosed blister pack station is further configured to receive the instructions from a third party and store the instructions in a cloud network. From the cloud network any other authorized blister pack station can download the instructions. This way, the instructions from a blister pack station may be transferred and stored in the other authorized blister pack station.

The disclosed blister pack station is configured to receive a blister pack/pill dispenser including an MID tag, a circuit and a chip. The blister pack station may include one or more modules for receiving one or more instructions from a third party, reminding a user according to the instructions, communicating the instructions to other devices or cloud network, and blister pack/pill dispensers. The one or more device may include, but are not limited to, a server, a blister pack, a computing device, and cloud network. Further, the third party may include a central server, an authorized person like doctor, pharmacist, etc. Further, the third party can store instructions in the blister pack station either indirectly via a remote server or a computing device or directly.

The disclosed blister pack station may store information about medicine/tablets/pills stored in a blister pack/pill dispenser including but not limited to, batch number, date of manufacturing, dosage timing information, manufacturer information, uses, side effects, identification information and so forth.

The disclosed blister pack station includes a feedback module or a reminder module for providing a feedback or a reminder to a user such as, but not limited to, a patient. The feedback or the reminder may include at least one of an audio reminder, a video reminder message, and a text message on an associated mobile device in communication with the blister pack station. In some embodiments, the blister pack station provides a visual indication based on light emitting diodes or a luminescent coating of ink or suitable material on the blister pack station or on the circuit of the blister pack. In some embodiments, the blister pack station may comprise one or more batteries for providing power to the blister pack station. The batteries may be solar operated batteries.

The disclosed blister pack station is configured to program or re-program itself based on one or more events comprising such as, but not limited to, breakage of a blister pack contained in the blister pack station, a timing when the blister pack breaks or opens, a location of the blister pack/blister pack station, a time-zone, and so forth. For example, the blister pack station may adjust a timing of subsequent dosage as per the time of the dose taken recently. In some embodiments the blister pack station is configured to arrange/change the stored instructions based on a time or time zone information where the blister pack station is used. For example, if the blister pack station is Mid ally in United States of America (USA) so Mid ally instructions are fed into it according to the time zone of USA. Further, the bister pack station may determine where the blister pack station is for example, in which country or city in the world. If the blister pack station is used in another country like Australia then the blister pack station may change or arrange the pre-stored instructions according to the time zone of Australia. In some embodiments, the blister pack station is configured to check location of the blister pack station and/or blister pack parked in the blister pack station at regular intervals and may automatically arrange the instructions accordingly.

The disclosed blister pack station is configured to communicate the information to a central server so as to check whether the medicine in a blister pack parked or stored in the blister pack station is authentic/genuine or fake.

The disclosed blister pack station includes a chip for storing information such as, but not limited to, batch number, manufacturer, company name, expiry date, manufacturing date, uses, dosage, time for taking medicine, side-effects, and so forth of the medicine of a blister pack contained in a slot of the blister pack station. An authorized person can feed instructions comprising the information in the chip.

The disclosed blister pack station is configured to remind patient about timings of taking the medicines. In some embodiments, the blister pack station also reminds the patients in case patient takes more or less dosage of a particular medicine from the blister pack.

The present disclosure provides a smart medication system comprising a blister pack station and a web means or mobile application installed on a computing device through which the medication system can remind or inform a user about medication or other information via the disclosed blister pack station. The web means or the mobile application may be in communication with the blister pack station. Further, the user may receive audio message, video message, text message, and so forth via the web means or the mobile application about the medication based on one or more instructions stored in the blister pack station.

The disclosed blister pack station includes an input means configured to receive information from a third party comprising an authentic person such a patient or a doctor. Further, the blister pack station may comprise a chip for communicating the instructions to a central server or a web-based server. In some embodiments, the blister pack station communicates the instructions or information with the central server or the web-based server when one or more events occur. The events may include, but not limited to, breakage of a blister pack stored in the blister pack station. The central server in an embodiment may check if the medicine/pills/tablets in the blister pack is genuine and authentic or not, and accordingly a feedback may be provided to a user or a patient by the blister pack station.

The disclosed blister pack station is configured to connect to a mobile phone of a user like a patient. In some embodiments, the blister pack station may connect to the mobile phone via a mobile application. Further, the blister pack may provide reminders or the feedback to the patient on the mobile phone. The feedback may include at least one of an audio feedback, a video feedback, and a text feedback. The reminders may include at least one of an audio reminder, a video reminder, and a text reminder.

It will be understood that the devices and the databases referred to in the previous sections are not necessarily utilized together method or system of the embodiments. Rather, these devices are merely exemplary of the various devices that may be implemented within a computing device or the server device, and can be implemented in exemplary another devices, and other devices as appropriate, that can communicate via a network to the exemplary server device.

It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art, which are also intended to be encompassed by the following claims.

The above description does not provide specific details of manufacture or design of the various components. Those of skill in the art are familiar with such details, and unless departures from those techniques are set out, techniques, known, related art or later developed designs and materials should be employed. Those in the art are capable of choosing suitable manufacturing and design details.

The terminology used herein is for the purpose of describing particular embodiments only and is not intended to be limiting of the disclosure. It will be appreciated that several of the above disclosed and other features and functions, or alternatives thereof, may be combined into other systems, methods, or applications. Various presently unforeseen or unanticipated alternatives, modifications, variations, or improvements therein may subsequently be made by those skilled in the art without departing from the scope of the present disclosure as encompassed by the following claims.

What is claimed is:

1. A blister pack station comprising:
   at least one slot configured to receive at least one blister pack comprising one or more tablets, wherein
   the at least one blister pack includes a small hole on its edge,
   the at least one blister pack is configured to slide down in the at least one slot and lock into a latch of the blister pack station via the small hole on the edge of the at least one blister pack, and
   the blister pack station gets activated on sliding of the at least one blister pack inside the at least one slot;
   an input module configured to receive a plurality of instructions about medication from at least one third party;
   a reminder module comprising at least one of an audio module and a visual module configured to provide a reminder to a user based on the plurality of instructions;
   a self-programming module configured to arrange one or more instructions of the plurality of instructions based on one or more events; and
   a chip configured to:
   establish a connection with at least one of the at least one blister pack and the at least one third party; and
   communicate the plurality of instructions to at least one of the at least one blister pack and the at least one third party.

2. The blister pack station of claim 1, wherein the chip is further configured to communicate with at least one of a central server and a cloud based device when one or more events occurs.

3. The blister pack station of claim 1, wherein the one or more events comprising at least one of a breaking of at least one of the plurality of cavity, a time at which the cavity breaks, and a time zone, wherein the at least one third party comprising at least one of an authorized person, a server, a cloud based device, a computing device, a mobile phone application, a web-based application, another blister pack station, and a person.

4. The blister pack station of claim 1 is retrofittable and is configured to receive or connect to any type of blister pack.

5. The blister pack station of claim 3, wherein the authorized person comprising at least one of a doctor, a patient, the user, a pharmacist, a manufacturer of the medication, and a caretaker.

6. The blister pack station of claim 1, wherein the plurality of instructions and the at least one instruction comprising a timing for taking the one or more tablets, a date of manufacturing of the one or more tablets, a batch information of the one or more tablets, an expiry information of the one or more tablets, manufacturer information, and dosage information.

7. The blister pack station of claim 5, wherein the reminder module sends a reminder to the user via at least one of the computing device of the user, the audio module, and the visual module of the at least one blister pack.

8. The blister pack station of claim 5, wherein the chip is configured to:
   send a breakage information and information of the at least one blister pack to the server when the at least one blister pack breaks, wherein the server checks for an authenticity of the blister pack and the one or more tablets based on the breakage information and information of the blister pack, and information stored in the server; and
   receive authenticity information of the at least one of the one or more tablets and the blister pack parked in the at least one slot of the blister pack station from the server.

9. The blister pack station of claim 5, wherein the chip is further configured to wirelessly connect and communicate the plurality of instructions to the at least one of the server, the computing device, the device based in a cloud network, the blister pack, and the another blister pack station.

10. The blister pack station of claim 1 further comprising a database comprising pre-stored information about a plurality of medicines.

11. The blister pack station of claim 1, wherein the at least one blister pack comprises:
    a roll of foil with an RFID chip, substrate circuits covering each component and a printed coating configured to be illuminated once a circuit is powered to indicate the compartment to open;
    a circuit comprising one or more circuit connectors configured to connect to one or more connectors of the blister pack station, and receive one or more instructions from the blister pack station; and
    a ridge and notch to allow the blister pack station to slot and lock the at least one blister pack into a position where the one or more circuit connectors of the at least one blister pack are lined up and make contact with the one or more connectors of the blister pack station.

12. The blister pack station of claim 11, wherein the input module is further configured to automatically fetch blister pack information from the at least blister pack, wherein the chip is further configured to communicate the blister pack information to the server for fetching additional blister pack information about the at least one blister pack from the server.

13. The blister pack station of claim 12 further comprising a display module to display information and instructions.

14. A blister pack station comprising:
at least one slot configured to receive at least one blister pack comprising a plurality of tablets, wherein
the at least one blister pack includes a small hole on its edge,
the at least one blister pack is configured to slide down in the at least one slot and lock into a latch of the blister pack station via the small hole on the edge of the at least one blister pack, and
the blister pack station gets activated on sliding of the at least one blister pack inside the at least one slot;
an input module configured to receive and store one or more instructions from at least one third party, wherein the one or more instructions comprising a timing for taking the plurality of tablets, a date of manufacturing of the plurality of tablets, a batch information of the plurality of tablets, an expiry information of the plurality of tablets, and manufacturer information:
a database comprising pre-stored information about a plurality of medicines;
a reminder module configured to provide a reminder to a user about medication based on the one or more instructions, wherein the user receives a reminder on an associated computing device in communication with the blister pack station;
a self-programming module configured to arrange the one or more instructions of the medication based on one or more events; and
a chip configured to determine if the blister pack and the one or more tablets are authentic or not based on information of the blister pack and information stored in the blister pack station, wherein the reminder module notifies the user about the authenticity based on the determination;
wherein the blister pack station is retrofittable and is configured to receive or connect to any type of blister pack.

15. The blister pack station of claim 14, wherein the at least one third party comprising at least one of an authorized person, a server, a cloud based device, a computing device, a mobile phone application, a web-based application, another blister pack station, and a person, further wherein the authorized person comprising at least one of a doctor, a patient, the user, a pharmacist, a manufacturer of the medication, and a caretaker.

16. The blister pack station of claim 15 further comprising a display module to display information and instructions.

17. The blister pack station of claim 15, wherein the chip is further configured to wirelessly connect and communicate the plurality of instructions to the at least one of the server, the computing device, the device based in a cloud network, the blister pack, and the another blister pack station.

18. The blister pack station of claim 14, wherein the at least one blister pack comprises:
a roll of foil with an RID chip, substrate circuits covering each component and a printed coating configured to be illuminated once a circuit is powered to indicate the compartment to open;
a circuit comprising one or more circuit connectors configured to connect to one or more connectors of the blister pack station, and receive one or more instructions from the blister pack station; and
a ridge and notch to allow the blister pack station to slot and lock the at least one blister pack into a position where the one or more circuit connectors of the at least one blister pack are lined up and make contact with the one or more connectors of the blister pack station.

19. The blister pack station of claim 18, wherein the input module is further configured to automatically fetch blister pack information from the al least blister pack, wherein the chip is further configured to communicate the blister pack information to the server for fetching additional blister pack information about the at least one blister pack from the server.

20. The blister pack station of claim 19, wherein the reminder comprising at least one of an audio reminder, a visual reminder, a text reminder, a notification, and a haptic feedback.

* * * * *